(12) United States Patent
Neuberger et al.

(10) Patent No.: US 7,351,242 B1
(45) Date of Patent: Apr. 1, 2008

(54) ACTIVE ENDOSCOPIC PHOTODYNAMIC THERAPY DEVICES; SYSTEMS AND METHOD

(75) Inventors: Wolfgang Neuberger, Labuan (MY); Stefan Spaniol, Bonn (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 1327 days.

(21) Appl. No.: 09/611,144

(22) Filed: Jul. 6, 2000

(51) Int. Cl.
*A61B 18/18* (2006.01)

(52) U.S. Cl. .......................................... 606/14; 607/88

(58) Field of Classification Search ................ 600/101, 600/104, 108, 115, 116, 158, 178; 606/13–18, 606/22, 23, 46; 604/264; 607/88, 89, 92
See application file for complete search history.

(56) References Cited

U.S. PATENT DOCUMENTS

| | | | |
|---|---|---|---|
| 4,589,404 A | 5/1986 | Barath et al. | |
| 4,852,567 A * | 8/1989 | Sinofsky | 606/3 |
| 5,135,534 A | 8/1992 | Tulip | |
| 5,363,458 A | 11/1994 | Pan | |
| 5,370,649 A * | 12/1994 | Gardetto et al. | 606/17 |
| 5,429,635 A | 7/1995 | Purcell | |
| 5,431,647 A | 7/1995 | Purcell | |
| 5,468,238 A * | 11/1995 | Mersch | 606/15 |
| 5,540,676 A | 7/1996 | Freiberg | |
| 5,566,267 A | 10/1996 | Neuberger | |
| 5,782,896 A * | 7/1998 | Chen et al. | 607/88 |
| 5,800,478 A * | 9/1998 | Chen et al. | 607/88 |
| 6,033,431 A * | 3/2000 | Segal | 607/89 |
| 6,086,558 A * | 7/2000 | Bower et al. | 604/96.01 |
| 6,254,594 B1 * | 7/2001 | Berry | 606/2 |
| 6,290,712 B1 * | 9/2001 | Nordquis et al. | 607/88 |
| 6,364,831 B1 * | 4/2002 | Crowley | 600/175 |
| 7,066,930 B2 * | 6/2006 | Boll et al. | 606/15 |

* cited by examiner

*Primary Examiner*—Ahmed M Farah
(74) *Attorney, Agent, or Firm*—Bolesh J Skutnik; B J Associates

(57) ABSTRACT

An active endoscopic system is disclosed containing an electromagnetic radiation system located at the distal end of the endoscopic device allowing for variable intensity application of desired wavelengths in the application of Photo-Dynamic Therapy (PDT) over a broad area. The power sources are varied according to the needs of a specific application. Various attachments and configurations may be used to enhance performance of a desired application, including but not limited to multi-balloon systems for centering the apparatus or limiting the treatment area, fiber optics for directly viewing the treatment area, vacuum systems for waste removal, tubes for delivering aminolevulinic acid (ALA) or other photosensitizers, and other fiber optics for illumination of treatment area. A preferred embodiment for PDT employs a multitude of low wattage diodes at the distal end of the endoscope, a scattering glass, cooling channel, external cooling unit, an inflatable balloon with a reflective surface and a tube connected to an external pump for the delivery and removal of photosensitizers. Each diode is selected to emit the respective frequency needed to activate the selected photosensitizer. Alternatively, a range of diodes may be selected to maximize the activation of the photosensitizer. Other embodiments include a chemiluminescent light source at the distal end of the endoscope. Other electromagnetic sources include microwave or radio frequency devices. The prime benefit of this system is the placement of the radiation source at the distal end of the device to bring the light source directly to the desired site.

11 Claims, 3 Drawing Sheets

ACTIVE ENDOSCOPIC PHOTODYNAMIC THERAPY DEVICES; SYSTEMS AND METHOD

BACKGROUND OF THE INVENTION

1. Field of the Invention

The present invention relates to medical endoscopic devices, and optoelectronics and in particular a diffuse electromagnetic radiation system located at the distal end of the endoscopic device useful for PhotoDynamic Therapy (PDT).

2. Invention Disclosure Statement

PDT generally relies on exposing a presensitized area to a selected wavelength of activating radiation. The activating radiation typically comes from a diode laser. A diffuse source of radiation can expose a greater area to activation energy and therefore necrotize a larger area. A diffuse light in the human body has conventionally been created with a diffuser or other such attachment to the distal end of an optical fiber. (e.g. U.S. Pat. Nos. 5,431,647; 5,429,635; 5,363,458). The power and light source are both external which requires that the transmission fiber be coupled to the source. The process and mechanisms of coupling often results in a loss of the energy emitted by the source. Therefore, these devices are prone to a loss of efficiency due to coupling problems. Once transmitted, the emitting light from the fiber possesses a narrow NA, limited dispersion and a single axial component. To compensate the light must be diffused with a diffuser. The diffuse light created by scattering is limited by the characteristics of light traveling through the delivery fiber and it is prone to problems such as uneven distribution of light and hotspots.

Endoscopic devices require coupling an electromagnetic radiation source to a fiber so that the radiation may be brought to the desired treatment area. Examples of these devices are the laser endoscopes found in U.S. Pat. Nos. 4,589,404; 5,135,534; 5,540,676. The process of coupling the fiber to the source generally results in a loss of efficiency and power. Also, coupling usually changes the characteristics of the irradiated light from the source. The resultant emission from the fiber is a beam with a small NA, high coherency, and narrow coverage area. The application of PDT with current technology is often a laborious process due to the limited treatment area created by the fiber. A diffuse electromagnetic source ideally would be able to treat a larger area.

An endoscopic device which does place a radiation source at the distal end of the device, is demonstrated in U.S. Pat. No. 5,468,238. The referenced device places a single diode laser at the distal end to maintain spatial coherency and to reduce the loss of power; however, this device is limited in application. If applied for PDT purposes, a narrow light source makes the procedure slow and inefficient. The source of the light is limited to the single diode and therefore is limited to a single wavelength. Flexibility in the types of sources would create broader applicability for a device.

Another device is demonstrated in U.S. Pat. No. 4,852,567. This laser tipped catheter solves the problem of wavelength transmission limitations in silica fibers. By placing a laser crystal at the distal end of the catheter, electromagnetic radiation of one wavelength of light may be converted to another more desired wavelength which is not transmittable through silica fibers. This system still places the initial power source external to the end of the catheter and will suffer from a loss of power due to coupling. The main focus of this invention is the conversion of wavelengths of one radiation source to a different wavelength which a normal optical fiber could not transmit. This invention does not create a diffuse light source. The placement of a laser crystal at the distal end of the fiber does not suggest placement of an actual electromagnetic source at the end of an endoscopic device. This system also limits the area of PDT application due to the narrowly emitted beam.

It would be useful and more efficient to have a source, which provides evenly diffuse radiation and can irradiate a broad area with diffuse radiation. It would also be useful to have a radiation source at the distal end of the endoscopic device to increase efficiency and control. It would be additionally useful to place multiple light sources at the distal end to have the possibility of multiple wavelengths and a greater consistency to the light. The utility of these features would be further increased by circumventing the transmission limitations of fiber optics. The prior art contains only limited solutions to some of these problems. The present invention addresses all these problems.

BRIEF SUMMARY AND OBJECTIVES OF THE INVENTION

It is an object of the present invention to provide an endoscopic system which has a diffuse source of electromagnetic radiation at the distal end of the device suitable for broader treatment areas in such applications as PDT.

It is another object of the present invention to provide a system which can utilize a wide range of illumination options not limited to laser technology.

Briefly stated the present invention provides an active endoscopic system which contains an electromagnetic radiation means located at the distal end of the endoscopic device allowing for variable intensity application of desired wavelengths in the application of PhotoDynamic Therapy (PDT) over a broad area. The power sources are varied according to the needs of a specific application. Various attachments and configurations may be used in conjunction with the endoscopic device to enhance performance of a desired application. Such enhancements may include but are not limited to multi-balloon systems for centering the apparatus or limiting the treatment area, fiber optics for directly viewing the area of treatment, vacuum systems for the removal of waste product, delivery tubes for the delivery of aminolevulinic acid (ALA) or other photosensitizers, and other fiber optics for illumination of treatment area. A preferred embodiment of this system for use in PDT employs a multitude of low wattage diodes at the distal end of the endoscope, a scattering glass, cooling channel, external cooling unit, an inflatable balloon with a reflective surface, a tube connected to an external pump for the delivery and removal of photosensitizers. Each diode is selected to emit the respective frequency needed to activate the selected photosensitizer. Alternatively, a range of diodes may be selected to maximize the activation of the photosensitizer. Other embodiments include a double walled balloon fed through a channel of an endoscope which would allow mixing of chemiluminescent chemicals as an alternative light source within the channel between the balloons. Still other embodiments include different electromagnetic sources for the emission of microwaves or radio frequencies. The prime benefit of this invention is the placement of the electromagnetic radiation source at the distal end of the device to bring the light source directly to the desired site.

DETAILED DESCRIPTION OF PREFERRED EMBODIMENTS

Figure 1:
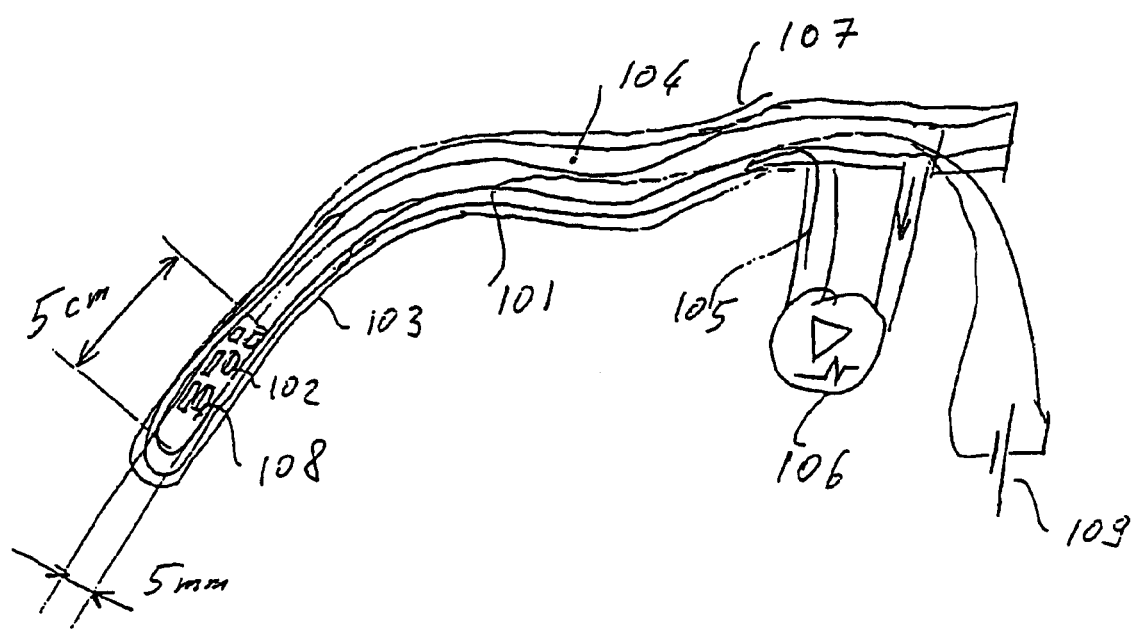
FIG. 1 shows a preferred embodiment of an endoscopic device with multiple diodes at the distal end of the device.
Figure 2:
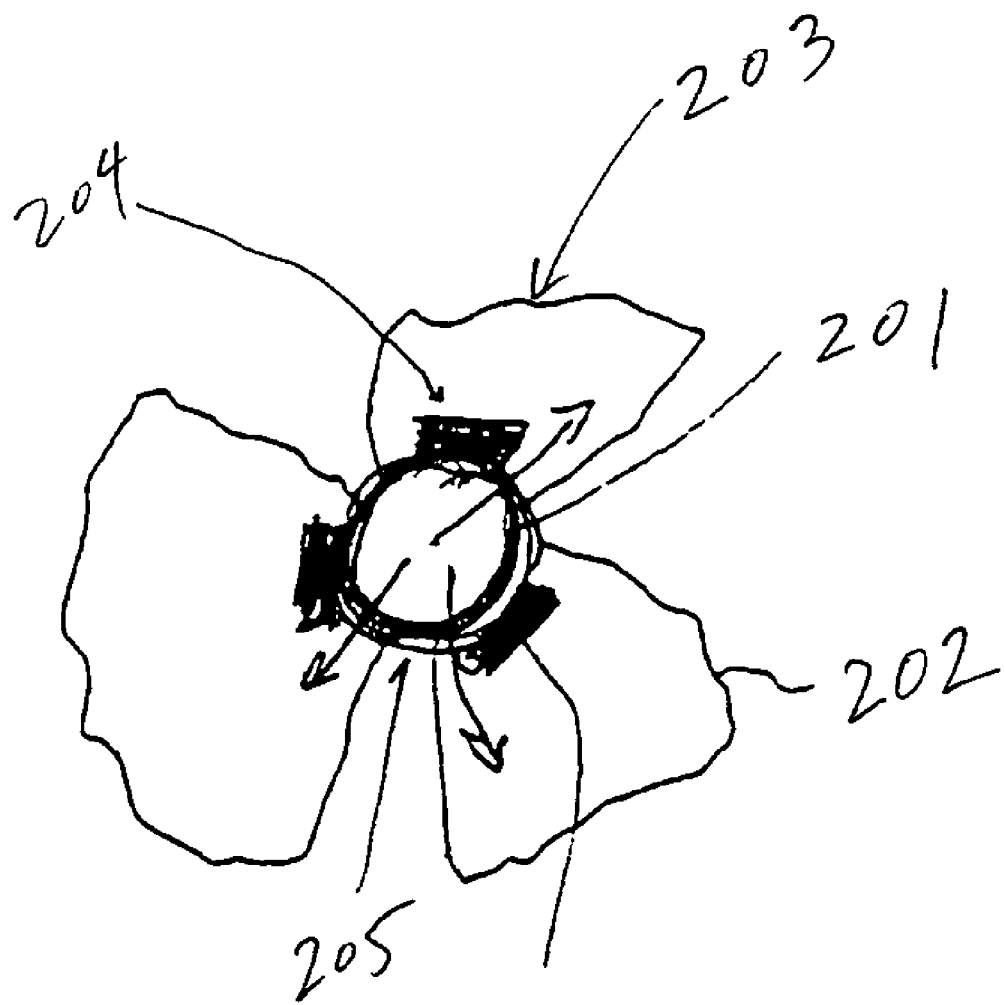
FIG. 2 shows a cross section of an endoscopic device with multi-diodes and a center channel.
Figure 3:
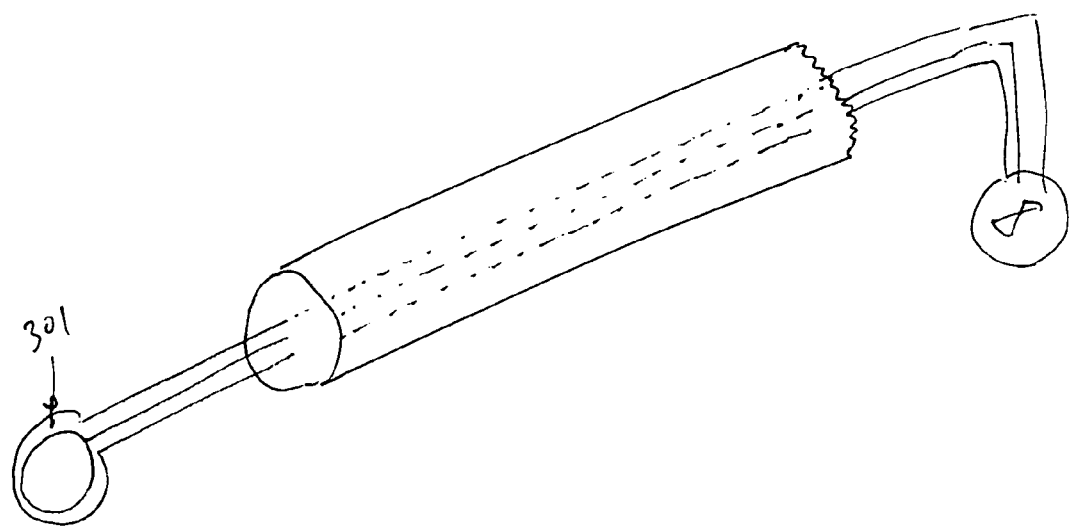
FIG. 3 shows a double walled balloon endoscopic device for use in chemiluminescent radiation.

The present invention provides an endoscopic system, which generates electromagnetic radiation directly at the desired site. Placing the electromagnetic radiation source at the distal end of the endoscopic device allows the device to be placed in an endoscope and moved to the desired site. This configuration has many advantages over prior art whose radiation transmission fiber optic transmission of radiation to a site. The power source to which the fiber is attached creates light in wide dispersion, multi-wavelength, multi-amplitude, and in many axial orientation. Coupling the fiber to the source can be very difficult. The energy being emitted by the laser needs to funneled into the narrow fiber and often this results in a loss of energy. One approach to increasing the efficiency in coupling is seen in U.S. Pat. No. 5,556,267. The core is shaped into a rectangular form to create a larger surface area maximizing the capture area of light. A coupled fiber inherently imposes certain light characteristics in transmitting the light through the fiber and therefore the output light is then limited to those same characteristics. A fiber depending on the respective refraction indices of the cladding and core allows only certain light to be transmitted through the fiber. The transmitted light will have similar wavelengths, axial orientation, and intensity. Once the light is transmitted, it must be deflected by a diffuser to create diffuse light.

A distally placed source takes full advantage of the emission characteristic of the source as compared to a coupled fiber. A distally placed source such as a diode can have larger numerical aperture (NA), broader dispersion, higher optical efficiency and wider spectrum of radiation as compared to electromagnetic radiation brought through optical fiber.

One type of a source which can be placed at the distal end of a device is a group of laser diode or a pattern of laser diode arrays. Diodes of a specific wavelength are preselected and placed externally at the end of the endoscopic device. The placement of a multitude of diodes at the distal end creates several advantages over standard fiber optics in light quality. The diodes used may be operated at lower wattage because there is no loss due to coupling. With the lower wattage comes the advantages of longer life, greater stability and cooler operation of the diodes. The diodes also have a natural dispersion pattern with one axis spreading more quickly than the other does. An optical fiber by its nature carries a more limited range of light and in the process of coupling to a diode will only output a smaller NA than the diode emits and transmit a smaller portion of energy created by the source. The diode will have a wider dispersion compared to the same light coming from an optical fiber and therefore will not be as prone to the problems with dispersion glass and fiber combination.

An alternative source of electromagnetic radiation in the UV to visible range is chemiluminescence. Through the use of a double walled balloon, chemiluminscent chemicals may be mixed at the distal end of an endoscopic device. The photons emitted from a chemical reaction encompass a broad spectrum.

Yet another alternative source of electromagnetic radiation which can be used in this system is miniature radio frequency or microwave generator. Certain moieties and reactions are activated through the use of energies in these regions.

The present invention is further illustrated by the following examples, but is not limited thereby.

EXAMPLE 1

An active endoscopic PDT device for mesotetrahydroxyphenylchlorin (mTHPC) treatment of the Esophagus.

A reasonably flexible cylindrical radiation device consists of a body (101) on which approximately 150 LED's (with a center line emission of 653 nm) are mounted. The LED emission surfaces (102) are protected by a scattering glass (108). An external tube (103) blocks undesired wavelengths (example <630 and >670) and defines an annular channel (104) to cool the LED's. Coolant (105) flows to an external cooler (106). The device is powered electronically (109) with 30 W (30 v, 1 A). It irradiates with a total useful energy of approximately 200 mW and an extra disposable jacket tube (107) is provided. For a fiber tip of 5 mm diameter×5 cm length a surface area of approximately 785 sq mm is provided to place diodes on. Diodes at the furthest distal end maybe placed at and angle to increase the area of irradiation even further and provide radiation forward direction.

EXAMPLE 2

An Active endoscopic PDT Device for the stomach using BenzoPorphyrin Derivatives (BPD) at 682 nm. A laser diode (204) of 1 W output from its 2 emissions surfaces is grounded on a water-cooled small heatsink and centered and incorporated in an inflatable balloon (202)(203) whose outside surface is partially reflective to homogenize the irradiation energy. 2V and 1-2A are sufficient to drive the device. The balloons are fed through a center channel (201). An external expandable sheath (205) may be used for flexibility reasons. Further embodiments of the invention may include devices powered by chemical luminescence, microwave and RF.

EXAMPLE 3

An inflatable double walled balloon is used for irradiating an internal organ (such as bladders). The space between the inner and outer balloon (301) is filled with chemiluminescence liquid that can be externally replenished. Spent and depleted liquid are externally discharged.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. An active endoscopic PhotoDynamic Therapy (PDT) device comprising:
   a distal and a proximal end;
   a radiation source positioned at said distal end;
   wherein said source provides a widely disperse radiation pattern across a section of body tissue, which section is large compared to said endoscopic device's distal cross section, and which body tissue is in proximity to said distal end;
   wherein said radiation source operates at a pre-selected wavelength and power range compatible with requirements of a preselected PDT drug; and,
   wherein said radiation source is powered remotely and said disperse radiation pattern is regulated in geometric distribution and wavelength by inputs at said proximal end and selection of sources at said distal end.

2. The active endoscopic device according to claim 1, wherein said radiation source is a multitude of diodes mounted on said device's distal end so as to create a widely disperse, broad spectrum illumination pattern to effectively irradiate a selected treatment site.

3. The active endoscopic device according to claim 2, wherein said diodes are diode lasers.

4. The active endoscopic device according to claim 3, wherein said diode lasers comprise lasers operating at different wavelengths.

5. The active endoscopic device according to claim 1, wherein said radiation source is provided by chemiluminescence, said chemiluminescence activating said selected PDT drug and originating at the distal end of said device.

6. The active endoscopic device according to claim 1, further comprising cooling means.

7. The active endoscopic device according to claim 1, further comprising means for delivering a substance which will be activated by said radiation.

8. The active endoscopic device according to claim 1, further comprising at least one balloon to serve as a centering mechanism.

9. The active endoscopic device according to claim 8, wherein a homogenizing means is provided, which is a partially reflective coating on said at least one balloon.

10. A method of performing PhotoDynamic Therapy with an active endoscopic device as in claim 1, comprising the steps of:
    selecting radiation sources with widely disperse, broad spectrum which are placed externally at a distal end of an active endoscopic device;
    positioning a catheter/endoscope into a patient and directing it to a predetermined treatment site within said patient;
    placing said active endoscopic device into said endoscope/catheter and advancing it so that its distal end with its radiation source and at a distal end of said endoscope; and
    energizing said radiation source and irradiating said selected treatment site for times and periods to achieve said PDT treatment for said selected treatment sites.

11. The active endoscopic device according to claim 2, wherein a homogenizing means is provided, which is a partially reflective film over said multitude of diodes.

* * * * *